United States Patent
Chen et al.

(10) Patent No.: US 11,833,133 B2
(45) Date of Patent: Dec. 5, 2023

(54) SOLID ORAL PHARMACEUTICAL COMPOSITION

(71) Applicant: Orient Pharma Co., Ltd., Taipei (TW)

(72) Inventors: Chien-Yu Chen, Taoyuan (TW); David Wong, Taoyuan (TW); Mongkol Sriwongjanya, Taoyuan (TW)

(73) Assignee: ORIENT PHARMA CO., LTD., Taipei (TW)

( * ) Notice: Subject to any disclaimer, the term of this patent is extended or adjusted under 35 U.S.C. 154(b) by 0 days.

(21) Appl. No.: 17/394,444

(22) Filed: Aug. 5, 2021

(65) Prior Publication Data

US 2022/0047547 A1 Feb. 17, 2022

Related U.S. Application Data

(60) Provisional application No. 63/064,954, filed on Aug. 13, 2020.

(30) Foreign Application Priority Data

Jan. 18, 2021 (TW) ................................ 110101784

(51) Int. Cl.

| | | |
|---|---|---|
| *A61K 31/397* | (2006.01) | |
| *A61K 31/47* | (2006.01) | |
| *A61K 9/00* | (2006.01) | |
| *A61K 47/02* | (2006.01) | |
| *A61K 9/48* | (2006.01) | |
| *A61K 47/12* | (2006.01) | |
| *A61K 47/32* | (2006.01) | |

(52) U.S. Cl.
CPC .......... *A61K 31/397* (2013.01); *A61K 9/0053* (2013.01); *A61K 9/485* (2013.01); *A61K 9/4808* (2013.01); *A61K 9/4858* (2013.01); *A61K 9/4866* (2013.01); *A61K 31/47* (2013.01); *A61K 47/02* (2013.01); *A61K 47/12* (2013.01); *A61K 47/32* (2013.01)

(58) Field of Classification Search
CPC .. A61K 31/397; A61K 9/0053; A61K 9/4808; A61K 9/485; A61K 9/4858; A61K 9/4866; A61K 31/47; A61K 47/02; A61K 47/12; A61K 47/32
See application file for complete search history.

(56) References Cited

U.S. PATENT DOCUMENTS

| | | | | |
|---|---|---|---|---|
| 2004/0126423 A1* | 7/2004 | Moore | ................... | A61K 31/35 514/460 |
| 2007/0032467 A1* | 2/2007 | Aoki | ....................... | A61P 43/00 514/460 |
| 2007/0160666 A1* | 7/2007 | Moore | ................. | A61K 9/2018 424/464 |
| 2013/0310420 A1* | 11/2013 | Hsiao | ..................... | A61K 33/08 514/311 |

FOREIGN PATENT DOCUMENTS

| | | |
|---|---|---|
| CN | 103340852 A | 10/2013 |
| TW | 200714280 A | 4/2007 |
| WO | WO-2014027334 A2 * 2/2014 | ........... A61K 31/549 |

OTHER PUBLICATIONS

Min Yu, Chunshui Liang, Qianran Kong, Yihan Wang and Minmin Li, Efficacy of combination therapy with ezetimibe and statins versus a double dose of statin monotherapy in participants with hypercholesterolemia: a meta-analysis of literature, Yu et al. Lipids in Health and Disease (2020) 19:1.

* cited by examiner

*Primary Examiner* — Robert A Wax
*Assistant Examiner* — Olga V. Tcherkasskaya
(74) *Attorney, Agent, or Firm* — BACON & THOMAS, PLLC

(57) ABSTRACT

A solid oral pharmaceutical composition is disclosed, which comprises: a first active ingredient, which is pitavastatin or a pharmaceutically acceptable salt thereof; a second active ingredient, which is ezetimibe or a pharmaceutically acceptable salt thereof; and at least one excipient, including a diluent, a stabilizing agent, a disintegrant, a binding agent, a sweetener, a lubricant, a glidant, a flavor, a coloring agent or a combination thereof.

16 Claims, 1 Drawing Sheet

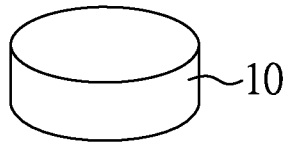 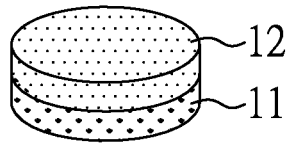 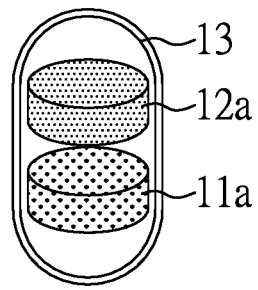
FIG. 1  FIG. 2  FIG. 3
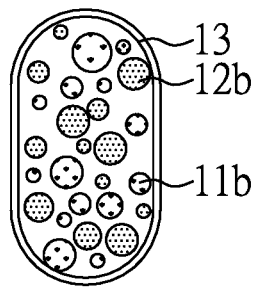 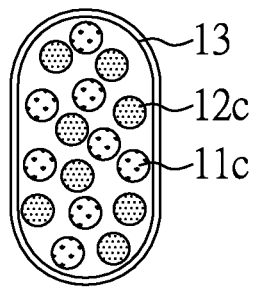
FIG. 4  FIG. 5
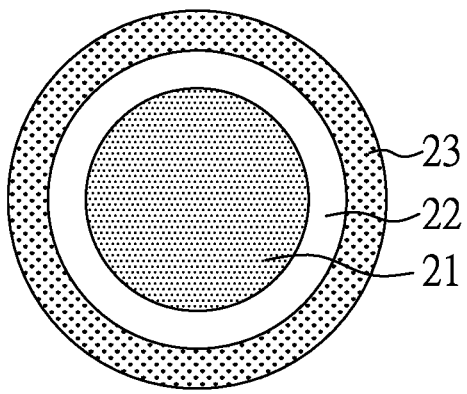
FIG. 6

SOLID ORAL PHARMACEUTICAL COMPOSITION

CROSS REFERENCE TO RELATED APPLICATION

This application claims the benefits of the Taiwan Patent Application Serial Number 110101784, filed on Jan. 18, 2021, the subject matter of which is incorporated herein by reference.

This application claims the benefit of filing date of U.S. Provisional Application Ser. No. 63/064,954, filed Aug. 13, 2020 under 35 USC § 119(e)(1).

BACKGROUND

1. Field

The present disclosure relates to a solid oral pharmaceutical composition and, more particularly, to a solid oral pharmaceutical composition comprising pitavastatin or a pharmaceutically acceptable salt thereof and ezetimibe or a pharmaceutically acceptable salt thereof in a unit dosage form.

2. Description of Related Art

Cerebral cardiovascular diseases include stroke, heart disease, high blood pressure and hyperlipidemia. These diseases have become the major cause of death in advanced countries in recent years. The number of deaths from cardiovascular diseases in Taiwan is the second to fourth among the top ten causes of death.

Hyperlipidemia is an important risk factor for cardiovascular disease. The accumulation of cholesterol and oxidized fat in the blood causes the pore size of the blood vessels to become smaller. The heart must increase the strength to transport blood, which will increase blood pressure and increase systolic blood pressure. The pressure of the surrounding blood vessels is thus increased, leading to hypertrophy of the left ventricle, abnormally increased blood pressure, and even the risk of atherosclerosis.

Poor living habits are an important factor in causing hyperlipidemia. Good and regular exercises can help increase the body's good cholesterol (high-density lipoprotein, HDL) and reduce the blood cholesterol concentration. When the blood lipid value has exceeded the standard and cannot be relied on diet and exercise to reach the treatment purpose, the medication is needed. At present, pitavastatin or other statin drugs are commonly used lipid-lowering drugs.

In recent years, in the clinical treatment of lowering blood lipids, it has gradually been discovered that only a single lipid-lowering drug may not be enough to achieve a satisfactory effect of controlling blood lipids. Therefore, there are currently studies in which pitavastatin or other statin drugs are combined with ezetimibe to improve the therapeutic effect.

However, when these two active ingredients are administered to patients in separated dosage forms, it is not only inconvenient to take for patients, but also prone to problems with improper dosage control. Therefore, it is desirable to provide a composition comprising two active ingredients in a unit dosage form to solve the aforesaid problems and improve the therapeutic effect.

SUMMARY

The present disclosure provides a solid oral pharmaceutical composition, wherein pitavastatin or a pharmaceutically acceptable salt thereof and ezetimibe or a pharmaceutically acceptable salt thereof are comprised in a single unit dosage form. In addition, the solid oral pharmaceutical composition the present disclosure can be used for treating or preventing cardiovascular diseases (for example, atherosclerosis) or related conditions.

The solid oral pharmaceutical composition of the present disclosure comprises: a first active ingredient, which is pitavastatin or a pharmaceutically acceptable salt thereof; a second active ingredient, which is ezetimibe or a pharmaceutically acceptable salt thereof; and at least one excipient, including a diluent, a stabilizing agent, a disintegrant, a binding agent, a sweetener, a lubricant, a glidant, a flavor, a coloring agent or a combination thereof.

In the solid oral pharmaceutical composition of the present disclosure, pitavastatin or a pharmaceutically acceptable salt thereof and ezetimibe or a pharmaceutically acceptable salt thereof are comprised in a single unit dosage form. Some studies indicate that pitavastatin calcium plus ezetimibe benefits patients with acute coronary syndrome (ACS). In addition, pitavastatin calcium plus ezetimibe reduces low-density lipoproteins (LDL) and total cholesterol (TC) more than pitavastatin calcium alone in ACS patients. In addition, some studies indicate that ezetimibe plus pitavastatin calcium in ACS patients with dyslipidemia decreased sitosterol levels more than statin therapy alone, wherein plasma sitosterol elevations are associated with an increased risk of coronary events in patients with coronary heart disease. Furthermore, some studies indicate that pitavastatin calcium plus ezetimibe prevents kidney dysfunction in nephrectomized rats fed high-cholesterol, wherein ezetimibe confers renoprotective effects by inhibiting cholesterol absorption, and pitavastatin calcium additively ameliorates kidney damage by increasing NO production via mechanisms independent of cholesterol reduction. Moreover, some studies indicate that co-administration of ezetimibe 10 mg/day enhances proteinuria-lowering effects of pitavastatin calcium 2 mg/day in chronic kidney disease patients by decreasing TC and triglyceride (TG) partly via a cholesterol-independent manner.

However, when these two active ingredients are administered to patients in separated dosage forms, it is not only inconvenient to take for patients, but also prone to problems with improper dosage control. Therefore, the solid oral pharmaceutical composition of the present disclosure is formulated into a solid oral formation with a single dosage form, so the patients can take two active ingredients with appropriate doses at once. In addition to the faster dispensing of medicines, it can also improve the convenience of patients taking medicines.

In the solid oral pharmaceutical composition of the present disclosure, the first active ingredient may be pitavastatin calcium, and the second active ingredient may be ezetimibe.

In the solid oral pharmaceutical composition of the present disclosure, a loading of the first active ingredient in a unit dosage form may be in a range from 0.5 mg to 5 mg, for example, about 2 mg.

In the solid oral pharmaceutical composition of the present disclosure, a loading of the second active ingredient in a unit dosage form may be in a range from 5 mg to 20 mg, for example, about 10 mg.

In the solid oral pharmaceutical composition of the present disclosure, the excipient may include a stabilizing agent, which may be magnesium oxide, magnesium aluminometasilicate, potassium hydroxide, sodium bicarbonate, sodium carbonate, sodium hydroxide, calcium carbonate, ammonium hydroxide, diethanolamine or a combination thereof.

The aforesaid stabilizing agent is an alkaline stabilizing agent, which can effectively stabilize pitavastatin or a pharmaceutically acceptable salt thereof, and in particular effectively stabilize pitavastatin calcium.

In the solid oral pharmaceutical composition of the present disclosure, the excipient may include another stabilizing agent, which may be citric acid, acetic acid, tartaric acid, lactic acid, sodium phosphate monobasic or a combination thereof. The aforesaid stabilizing agent is an acidic stabilizing agent, which can effectively stabilize ezetimibe or a pharmaceutically acceptable salt thereof, and in particular effectively stabilize ezetimibe.

The type of the solid oral pharmaceutical composition of the present disclosure can be any type known in the art, such as tablets, granules or capsules. When the solid oral pharmaceutical composition is a tablet or a granule, the tablet or the granule may comprise a protection layer, and the material of the protection layer may comprise a polymer such as povidone. In addition, the number of the protection layers is not particularly limited, and can be a single layer or multiple layers of the protection layers.

In one embodiment of the present disclosure, the solid oral pharmaceutical composition may be a single layered tablet, which comprises the first active ingredient, the second active ingredient and the excipient. For example, the single layered tablet may comprise about 2 mg of pitavastatin calcium, about 10 mg of ezetimibe and suitable excipient.

In another embodiment of the present disclosure, the solid oral pharmaceutical composition may be a double layered tablet, wherein one layer of the double layered tablet may comprise the first active ingredient and the excipient, and the other layer of the double layered tablet may comprise the second active ingredient and the excipient. Herein, the excipients comprised in these two layers may be the same or different, depending on the drug design. For example, one layer may comprise about 2 mg of pitavastatin calcium and suitable excipient, and the other layer may comprise about 10 mg of ezetimibe and suitable excipient.

In another embodiment of the present disclosure, the solid oral pharmaceutical composition may be a capsule, wherein the aforesaid first active ingredient and the aforesaid second active ingredient can be separately prepared into two independent tablets or granules, and then the prepared independent tablets or granules with appropriate doses are inserted into one capsule.

In another embodiment of the present disclosure, the solid oral pharmaceutical composition may be a capsule, and a first tablet and a second tablet are comprised inside the capsule. Herein, the first tablet may comprise the first active ingredient and the excipient, and the second tablet may comprise the second active ingredient and the excipient. The excipients comprised in the first tablet and the second tablet may be the same or different, depending on the drug design. For example, the first tablet may comprise about 2 mg of pitavastatin calcium and suitable excipient, and the second tablet may comprise about 10 mg of ezetimibe and suitable excipient.

In another embodiment of the present disclosure, the solid oral pharmaceutical composition may be a capsule, and a first granule and a second granule are comprised inside the capsule. Herein, the first granule may comprise the first active ingredient and the excipient, and the second granule may comprise the second active ingredient and the excipient. The excipients comprised in the first granule and the second granule may be the same or different, depending on the drug design. For example, the first granule(s) comprised in the capsule may comprise total dose of about 2 mg of pitavastatin calcium and suitable excipient, and the second granule(s) comprised in the capsule may comprise total dose of about 10 mg of ezetimibe and suitable excipient.

In one embodiment of the present disclosure, the first granule may be prepared by direct granulation of the first active ingredient and the excipient, and the second granule may be prepared by direct granulation of the second active ingredient and the excipient. Hence, the first granule and the second granule may not have specific structures.

In another embodiment of the present disclosure, the solid oral pharmaceutical composition may be a capsule, and a first pellet and a second pellet are comprised inside the capsule. Herein the first pellet may comprises a core-shell structure, which may comprise: a first core; a first drug-containing layer disposed on the first core and comprising the first active ingredient and the excipient; and a first protection layer disposed on the first drug-containing layer and comprising a polymer. Herein, the first drug-containing layer covers the whole surface of the first core, and the first protection layer covers the whole surface of the first drug-containing layer. The first active ingredient may be pitavastatin calcium. The excipient may be the aforesaid alkaline stabilizing agent. In one embodiment of the present disclosure, the used alkaline stabilizing agent may be magnesium oxide, but the present disclosure is not limited thereto. The used stabilizing agent may be varied according to the drug design. In addition, a weight ratio of the pitavastatin calcium and the alkaline stabilizing agent may be in a range from 20:1 to 1:1, 15:1 to 2:1, 10:1 to 3:1 or 7:1 to 3:1.

In addition, the second pellet may comprise a core-shell structure, which may comprise: a second core; a second drug-containing layer disposed on the second core and comprising the second active ingredient and the excipient; and a second protection layer disposed on the second drug-containing layer and comprising a polymer. Herein, the second drug-containing layer covers the whole surface of the second core, and the second protection layer covers the whole surface of the second drug-containing layer. The second active ingredient may be ezetimibe. The excipient may be the aforesaid acidic stabilizing agent. In one embodiment of the present disclosure, the used acidic stabilizing agent may be citric acid, but the present disclosure is not limited thereto. The used stabilizing agent may be varied according to the drug design. In addition, a weight ratio of ezetimibe to the acidic stabilizing agent may be in a range from 150:1 to 30:1, 120:1 to 50:1, 110:1 to 70:1 or 100:1 to 80:1.

Herein, the first core and the second core are respectively used as a carrier to carry the first drug-containing layer and the second drug-containing layer. Herein, the first core or the second core may respectively a sphere. For example, the first core and the second core may respectively be spheres made from sucrose and/or starch and/or microcrystalline cellulose. The size (in particular, the diameter) of the sphere may be in a range from 1700 µm to 250 µm, 1000 µm to 355 µm or 850 µm to 500 µm.

In addition, the first protection layer and the second protection layer may respectively protect the first core, the first drug-containing layer, the second core or the second drug-containing layer from damage by external stress. Herein, the polymer contained in the first protection layer or the second protection layer is not particularly limited, for example can be povidone. In addition, on the basis of the weight of the first protection layer or the second protection layer, the amount of povidone may be in a range from 1% to 50%, 5% to 30%, 10% to 25% or 15% to 20%.

In another embodiment of the present disclosure, the aforesaid first granule and second granule without specific structures can be used in combination with the aforesaid first pellet and second pellet with the core-shell structures. For example, the first granule without specific structures and the second pellet with the core-shell structure may be together inserted into one capsule, and vice versa.

In addition to the aforesaid solid oral pharmaceutical composition, the present disclosure further provides the use of the aforesaid solid oral pharmaceutical composition in treating or preventing cardiovascular diseases (for example, atherosclerosis).

Furthermore, the present disclosure further provides a method for treating or preventing cardiovascular diseases, which comprises: administering the aforesaid solid oral pharmaceutical composition to a subject in need thereof. The subject in need thereof can be the subject who needs to treat or prevent cardiovascular diseases.

In the present disclosure, the term "treating", "treat" or "treatment" refers to application or administration of the solid oral pharmaceutical composition to a subject with the purpose to cure, alleviate, relieve, alter, remedy, improve, or affect the disease, the symptom, or the predisposition.

Other novel features of the disclosure will become more apparent from the following detailed description when taken in conjunction with the accompanying drawings.

BRIEF DESCRIPTION OF THE DRAWINGS

FIG. 1 is a schematic diagram showing a solid oral pharmaceutical composition according to Example 1 of the present disclosure.

FIG. 2 is a schematic diagram showing a solid oral pharmaceutical composition according to Example 2 of the present disclosure.

FIG. 3 is a schematic diagram showing a solid oral pharmaceutical composition according to Example 3 of the present disclosure.

FIG. 4 is a schematic diagram showing a solid oral pharmaceutical composition according to Example 4 of the present disclosure.

FIG. 5 is a schematic diagram showing a solid oral pharmaceutical composition according to Example 5 of the present disclosure.

FIG. 6 is a cross-sectional view showing a first or second pellet according to Example 5 of the present disclosure.

DETAILED DESCRIPTION OF EMBODIMENT

Different embodiments of the present invention are provided in the following description. These embodiments are meant to explain the technical content of the present invention, but not meant to limit the scope of the present invention. A feature described in an embodiment may be applied to other embodiments by suitable modification, substitution, combination, or separation.

It should be noted that, in the present specification, when a component is described to have an element, it means that the component may have one or more of the elements, and it does not mean that the component has only one of the element, except otherwise specified.

Moreover, in the present specification, the ordinal numbers, such as "first" or "second", are used to distinguish a plurality of elements having the same name, and it does not means that there is essentially a level, a rank, an executing order, or an manufacturing order among the elements, except otherwise specified. A "first" element and a "second" element may exist together in the same component, or alternatively, they may exist in different components, respectively. The existence of an element described by a greater ordinal number does not essentially means the existent of another element described by a smaller ordinal number.

Herein, except otherwise specified, when it comes to feature A "or" or "and/or" feature B, it refers to the presence of A alone, B alone, or A and B exist at the same time. When it comes to feature A "and" feature B, it means that A and B exist at the same time. The term "comprise", "include", "have ", or "contain" means including but not limited thereto. Moreover, in the present specification, a value may be interpreted to cover a range within ±10% of the value, and in particular, a range within ±5% of the value, except otherwise specified; a range may be interpreted to be composed of a plurality of subranges defined by a smaller endpoint, a smaller quartile, a median, a greater quartile, and a greater endpoint, except otherwise specified.

Different embodiments of the present disclosure are provided in the following description. These embodiments are meant to explain the technical content of the present disclosure, but not meant to limit the scope of the present disclosure.

Unless otherwise specified, in the following preparation examples, examples and comparative examples, the temperature is shown by Celsius, the parts and percentages are shown by weight. The relationship between parts by weight and parts by volume is like the relationship between kilograms and liters.

Dissolution Methods and Assay

Dissolution medium such as 0.1N HCl, phosphate buffer (pH 4.5) and phosphate buffer (pH 6.8) were prepared following USP Method. 0.3% Tween 80 was added into the medium to help solubilize the active ingredients. Dissolution conditions were summarized as in the following. Dissolution samples were analyzed by HPLC method.

Apparatus: USP apparatus II (Paddle Method) with sinkers.

Medium: 0.1N HCl, Phosphate Buffer phosphate buffer (pH 4.5) or Phosphate Buffer phosphate buffer (pH 6.8).

Volume: 900 mL
Temperature: 37±0.5° C.
Filter: 10 μm HDPE full flow filter tips
Sampling Volume: 10 mL
Sampling Times: 5, 10, 15, 20, 30 and 45 minutes Example 1: Single Layered Table Component Pitavastatin calcium (10 mg), Ezetimibe (50 mg), lactose monohydrate (629 mg), microcrystalline cellulose (MCC) (308 mg), sodium lauryl sulfate (SLS) (10 mg), sodium starch glycolate (SSG) (90 mg), crospovidone (30 mg), magnesium stearate (8 mg) and povidone (45 mg), 95% alcohol (18 mg), and purified water (72 mg). Alcohol and water were evaporated during the drying process.

Manufacturing Process

Pitavastatin calcium, ezetimibe, lactose, microcrystalline cellulose (MCC), sodium lauryl sulfate (SLS), sodium starch slycolate (SSG) and povidone were discharged into a suitable container separately. A binding solution made of 45 mg povidone dissolved in 18 mg of alcohol and 72 gm water was prepared.

The pitavastatin calcium and ezetimibe were first mixed with SLS, MCC and SSG which have been passed through 30 mesh sieve by Comil and the mixture was rotated 100 times. The mixture was discharged with lactose. All materials were transferred into a granulator and mixed by the high shear mixer for 7 min (impeller 215 rpm).

After pre-mixing, the binder solution was added to the higher mixer, followed by granulating with Chopper 3400 rpm (impeller 215 rpm). The wet granules were dried at 40 to 60° C. The dried granules were mixed with sieved crospovidone and magnesium stearate for the final blending.

Tablets were compressed by rotatory tableting machine, and the schematic diagram of the target tablet 10 is shown in FIG. 1, wherein the weight of the target tablet was 300 mg±15 mg per unit and the hardness of final tablets was controlled within 8 to 11 kp. In addition, each tablet comprises about 2 mg of pitavastatin calcium and about 10 mg of ezetimibe.

The obtained tablets were tested with aforesaid dissolution test, and the results are shown in the following Table 1 and Table 2.

TABLE 1

| Drug | % Released into 0.1 N HCl with 0.3% Tween 80 at sampling time (min) | | | | |
|---|---|---|---|---|---|
| | 5 min | 10 min | 15 min | 30 min | 45 min |
| Pitavastatin Ca | 79% | 84% | 86% | 89% | 90% |
| Ezetimibe | 56% | 70% | 77% | 86% | 91% |

TABLE 2

| Drug | % Released into phosphate buffer (pH 6.8) with 0.3% Tween 80 at sampling time (min) | | | | |
|---|---|---|---|---|---|
| | 5 min | 10 min | 15 min | 30 min | 45 min |
| Pitavastatin Ca | 69% | 90% | 95% | 97% | 98% |
| Ezetimibe | 54% | 77% | 86% | 94% | 96% |

Example 2: Double Layered Table

Component of Pitavastatin Calcium Layer

Pitavastatin calcium (24 mg), lactose monohydrate (732 mg), microcrystalline cellulose (732 mg), magnesium oxide (96 mg), sodium starch glycolate (192 mg), crospovidone (76.8 mg), magnesium stearate (9.6 mg) and povidone (57.6 mg), 95% alcohol (57.6 mg), and water (57.6 mg). Alcohol and water were evaporated during the drying process.

Component of Ezetimibe Layer

Ezetimibe (120 mg), lactose monohydrate (720 mg), microcrystalline cellulose (950.4 mg), sodium lauryl sulfate (24 mg), sodium starch glycolate (38.4 mg), magnesium stearate (9.6 mg) and povidone (57.6 mg), 95% alcohol (57.6 mg), and water (57.6 mg). Alcohol and water were evaporated during the drying process.

Preparation of Pitavastatin Calcium Granules

Pitavastatin calcium, lactose monohydrate, microcrystalline cellulose, magnesium oxide (MgO), sodium starch glycolate, crospovidone, magnesium stearate and povidone were discharged into a suitable container separately. A binding solution was prepared by dissolving 57.6 gm povidone in a solution made of 57.6 gm alcohol and 57.6 gm water.

A geometric dilution method was used herein. The pitavastatin calcium was first mixed with MgO, part of MCC and part of SSG after passing through 30 mesh sieve by Comil. All materials for mixing were rotated by drum mixer for 100 times. Lactose which was delumped through mesh sieve by comil was discharged. All materials were transferred into a granulator and mixed using the high shear mixer for 7 min (impeller 215 rpm).

Then, the granulation was performed by turning on the impeller (215 rpm) and chopper (3,400 rpm). The binder solution was added into the granulator within 2 min in a planetary mixer for 3 minutes. The wet granules were dried at 50° C. in a try dryer until the water content of the granules was below 2.0% (measured as loss on drying at 105° C. for 15 min by IR Moisture Analyzer).

After drying, the dry granules were mixed with the rest of MCC, rest of SSC and crospovidone together by drum mixer with 300 times. For lubrication, the mixture granules were mixed with magnesium stearate by drum mixer with 60 times.

Preparation of Ezetimibe Granules

Ezetimibe, lactose monohydrate, microcrystalline cellulose, sodium lauryl sulfate, sodium starch glycolate, magnesium stearate and povidone were discharged into a container separately. A binding solution was prepared by dissolving 57 gm povidone in a solution made of 57 gm alcohol and 57 gm water.

The ezetimibe was first mixed with SLS, SSG and part of MCC after passing through 30 mesh sieve by Comil 032R and all materials for mixing were rotated by drum mixer for 100 times. Lactose which was delumped through 30 mesh sieve by comil was discharged. All materials were transferred into a granulator and mixed using the high shear mixer for 7 min (impeller 215 rpm).

Then, the granulation was performed by turning on the impeller (215 rpm) and chopper (3,400 rpm). The binder solution was added to the granulator within 2 min in a planetary mixer for 3 minute. The wet granules were dried at 50° C. in a tray dryer until the water content of the granules was below 2.0% (measured as loss on drying at 105° C. for 15 min by IR Moisture Analyzer).

After drying, the dry granules were mixed with the rest of MCC together by drum mixer with 300 times. For lubrication, the mixture granules were mixed with magnesium stearate by drum mixer with 60 times.

The obtained pitavastatin calcium granules and ezetimibe granules were compressed into double layered tablets using a double-side rotatory tableting machine. The schematic diagram of the target tablet is shown in FIG. 2, and the target tablet comprises: a pitavastatin calcium layer 11 and an ezetimibe layer 12. The target weight per unit was 320 mg±16 mg, and the hardness of tablet was controlled within 9 to 13 kp. In addition, each tablet comprises about 2 mg of pitavastatin calcium and about 10 mg of ezetimibe.

The obtained tablets were tested with aforesaid dissolution test, and the results are shown in the following Table 3 and Table 4.

TABLE 3

| Drug | % Released into 0.1 N HCl with 0.3% Tween 80 at sampling time (min) | | | | |
|---|---|---|---|---|---|
| | 5 min | 10 min | 15 min | 30 min | 45 min |
| Pitavastatin Ca | 81% | 87% | 89% | 86% | 89% |
| Ezetimibe | 30% | 56% | 67% | 79% | 83% |

TABLE 4

| | % Released into Phosphate Buffer (pH 6.8) with 0.3% Tween 80 at sampling time (min) | | | | |
|---|---|---|---|---|---|
| Drug | 5 min | 10 min | 15 min | 30 min | 45 min |
| Pitavastatin Ca | 90% | 96% | 97% | 99% | 100% |
| Ezetimibe | 42% | 72% | 80% | 88% | 91% |

Example 3: Tables in One Capsule

Component of Pitavastatin Calcium Tablet

Pitavastatin calcium (10 mg), lactose monohydrate (454 mg), pregelatinized starch (54 mg), magnesium aluminometasilicate (11 mg), magnesium stearate (3 mg) and hydroxypropyl methylcellulose (HPMC) (9 mg), 95% alcohol (40 mg), and water (40 mg). Alcohol and water were evaporated during the drying process.

Component of Ezetimibe Tablet

Ezetimibe (50 mg), lactose monohydrate (190 mg), microcrystalline cellulose (190 mg), sodium lauryl sulfate (10 mg), pregelatinized starch (50 mg), magnesium stearate (3 mg) and hydroxypropyl methylcellulose (8 mg), 95% alcohol (37 mg) and water (37 mg). Alcohol and water were evaporated during the drying process.

The pitavastatin calcium granules and the ezetimibe granules were prepared by the similar method described in Example 2.

The obtained pitavastatin calcium granules were compressed into single layer tablets using a rotatory tableting machine. The target weight per unit was 120 mg ±6 mg, and the hardness of tablet was controlled within 4 to 6 kp. In addition, the obtained ezetimibe granules were compressed into single layer tablets using a rotatory tableting machine. The target weight per unit was 100 mg±5 mg, and the hardness of tablet was controlled within 3 to 6 kp. Then, the obtained pitavastatin calcium tablet and the obtained ezetimibe table were inserted into one gelatin capsule manually. The schematic diagram of the obtained capsule is shown in FIG. 3, wherein the obtained capsule comprises: a pitavastatin calcium tablet 11a, an ezetimibe tablet 12a and a capsule 13. In addition, each capsule comprises about 2 mg of pitavastatin calcium and about 10 mg of ezetimibe.

Example 4: Granules in One Capsule

The pitavastatin calcium granules and the ezetimibe granules prepared in Example 2 were directly inserted into one gelatin capsule manually. The schematic diagram of the obtained capsule is shown in FIG. 4, wherein the obtained capsule comprises: pitavastatin calcium granules 11b, ezetimibe granules 12b and a capsule 13. In addition, each capsule comprises about 2 mg of pitavastatin calcium and about 10 mg of ezetimibe.

Example 4: Pellets in One Capsule

In the present example, the pitavastatin calcium pellet and the ezetimibe pellet respectively have the structure shown in FIG. 6. As shown in FIG. 6, the active ingredient pellet used in the present example comprises: a core 21; a drug-containing layer 22 disposed on the core 21 and covering the whole surface of the core 21; and a protection layer 23 disposed on the drug-containing layer 22 and covering the whole surface of the drug-containing layer 22. In the present example, the core 21 is a sphere, and the drug-containing layer 22 is a layer comprising pitavastatin calcium or ezetimibe.

Preparation of Pitavastatin Calcium Pellet

Drug-Containing Layer

Pitavastatin calcium (9 mg) was mixed and dispersed homogeneously with mannitol (24 mg), povidone (8 mg), magnesium oxide (2 mg), sodium lauryl sulfate (2 mg) in purified water. The mixture was stirred and homogenized until the suspension has no aggregations.

Protection Layer

Mannitol (47 mg), povidone (15 mg), talc (27 mg) and iron oxide yellow (0.5 mg) were mixed in purified water.

The fluidized bed equipment was used for pellet coating. After adding sugar balls (using sucrose as raw material spheres) into the preheated equipment, when the product temperature was above 35° C., the formulated suspension for the drug-containing layer was used to proceed the coating process of the drug-containing layer. In the subsequent coating process, the inlet gas temperature and the inlet gas volume were adjusted to control the product temperature to not exceed 60° C. After the coating process of the drug-containing layer, the formulated suspension for the protection layer was used to proceed the coating process of the protection layer. The coating process of the protection layer was continuously performed after the previous coating operation until the suspension of the protection layer was exhausted. After the coating process, the obtained pellets were dried, and about 2 mg of the pitavastatin calcium pellets were inserted into a capsule.

Preparation of Ezetimibe Pellet

Drug-Containing Layer

Ezetimibe (36 mg) was mixed and dispersed homogeneously with mannitol (80 mg), povidone (27 mg), anhydrous citric acid (0.4 mg), sodium lauryl sulfate (0.4 mg) in water. The mixture was stirred and homogenized until the suspension has no aggregations.

Protection Layer

Mannitol (38 mg), povidone (13 mg), talc (15 mg) and sodium lauryl sulfate (7 mg) were mixed in purified water.

The fluidized bed equipment was used for pellet coating. After adding sugar balls (using sucrose as raw material spheres) into the preheated equipment, when the product temperature was above 35° C., the formulated suspension for the drug-containing layer was used to proceed the coating process of the drug-containing layer. In the subsequent coating process, the inlet gas temperature and the inlet gas volume were adjusted to control the product temperature to not exceed 60° C. After the coating process of the drug-containing layer, the formulated suspension for the protection layer was used to proceed the coating process of the protection layer. The coating process of the protection layer was continuously performed after the previous coating operation until the suspension of the protection layer was exhausted. After the coating process, the obtained pellets were dried. About 10 mg of the ezetimibe pellets were inserted into the capsule comprising about 2 mg of the pitavastatin calcium pellets.

The schematic diagram of the composition comprising the pitavastatin calcium pellets and the ezetimibe pellets prepared in the present example is shown in FIG. 5, wherein the composition comprises: pitavastatin calcium pellets 11c, ezetimibe pellets 12c and a capsule 13. In addition, each capsule comprises about 2 mg of pitavastatin calcium and about 10 mg of ezetimibe.

The obtained capsules were tested with aforesaid dissolution test. The dissolution medium used herein respectively is medium containing 0.1 N HCl with 0.3% Tween 80, phosphate buffer (pH 4.5) with 0.3% Tween 80 and phosphate buffer (pH 6.8) with 0.3% Tween 80. The results are shown in the following Table 5 to Table 7.

TABLE 5

% Released into 0.1N HCl with 0.3% Tween 80 at sampling time (min)

| Drug | 5 min | 10 min | 15 min | 20 min | 30 min | 45 min |
|---|---|---|---|---|---|---|
| Pitavastatin Ca | 90% | 99% | 100% | 100% | 100% | 99% |
| Ezetimibe | 71% | 95% | 99% | 100% | 101% | 101% |

TABLE 6

% Released into Phosphate Buffer (pH 4.5) with 0.3% Tween 80 at sampling time (min)

| Drug | 5 min | 10 min | 15 min | 20 min | 30 min | 45 min |
|---|---|---|---|---|---|---|
| Pitavastatin Ca | 82% | 100% | 102% | 102% | 102% | 102% |
| Ezetimibe | 64% | 99% | 103% | 104% | 105% | 105% |

TABLE 7

% Released into Phosphate Buffer (pH 6.8) with 0.3% Tween 80 at sampling time (min)

| Drug | 5 min | 10 min | 15 min | 20 min | 30 min | 45 min |
|---|---|---|---|---|---|---|
| Pitavastatin Ca | 81% | 98% | 102% | 102% | 102% | 102% |
| Ezetimibe | 69% | 96% | 102% | 103% | 104% | 104% |

Stability of Pitavastatin Calcium

Pitavastatin calcium was found not stable. Thus, in the present disclosure, an alkaline agent (herein, magnesium oxide) was added into the formulation to stabilize pitavastatin calcium. Herein, the tablets having similar components described in Example 1 were used as the test samples.

The test samples packed in Alu-alu blisters were store under 55° C./75% RH. The results are shown in the following Table 8.

TABLE 8

| Sample | Time | Assay of pitavastatin calcium (%) |
|---|---|---|
| Without MgO | Initial | 94.3 |
| | One week | 91.3 |
| | Two weeks | 88.2 |
| With MgO | Initial | 96.3 |
| | One week | 94.7 |
| | Two weeks | 95.9 |

Note: Assay of pitavastatin calcium (%)=(Content of pitavastatin calcium of the test sample after storage/Content of pitavastatin calcium of the initial test sample)×100%

Stability of Ezetimibe

The stability of ezetimibe pellets with acidic agent (herein, citric acid) was measured herein. Herein, the capsules shown in Example 5 were used as the test samples. The capsules comprising ezetimibe pellets were stored under 40° C./75% RH and 55° C./75% RH, and detected by Waters Alliance HPLC system with UV 245 nm. The amounts of the impurities were measured by liquid chromatography (Hypersil Gold C18). The formulations and the results are shown in the following Table 9.

TABLE 9

| Formulation of the pellets and contents of each components | Content of the citric acid in the formulation | Storage condition | Major impurity (%) | Total impurity (%) |
|---|---|---|---|---|
| Sugar sphere, 100.0 mg/unit | 0 mg/unit | Initial | 0.05 | 0.1 |
| Ezetimibe, 10.0 mg/unit | | 5 Days/55° C. | 0.62 | 0.8 |
| Mannitol, 32.9 mg/unit | | 1 Month/40° C. | 0.07 | 0.2 |
| Povidone, 11.0 mg/unit | 0.10 mg/unit | Initial | 0.04 | 0.1 |
| Sodium Lauryl Sulfate, 2.0 mg/unit | | 5 Days/55° C. | 0.18 | 0.2 |
| Talc, 4.1 mg/unit | | 1 Month/40° C. | 0.07 | 0.1 |
| Sugar sphere, 100.0 mg/unit | 0.05 mg/unit | Initial | 0.06 | 0.2 |
| Ezetimibe, 10.0 mg/unit | | 5 Days/55° C. | 0.20 | 0.4 |
| Mannitol, 32.2 mg/unit* | | 1 Month/40° C. | 0.05 | 0.1 |
| Povidone, 10.7 mg/unit | 0.10 mg/unit | Initial | 0.05 | 0.2 |
| Tween 80, 2.0 mg/unit | | 5 Days/55° C. | 0.18 | 0.4 |
| Talc, 5.0 mg/unit | | 1 Month/40° C. | 0.06 | 0.2 |
| | 0.20 mg/unit | Initial | 0.06 | 0.2 |
| | | 5 Days/55° C. | 0.22 | 0.4 |
| | | 1 Month/40° C. | 0.05 | 0.2 |
| | 0.35 mg/unit | Initial | 0.06 | 0.1 |
| | | 5 Days/55° C. | 0.37 | 0.4 |
| | | 1 Month/40° C. | 0.12 | 0.2 |
| | 0.70 mg/unit | Initial | 0.06 | 0.1 |
| | | 5 Days/55° C. | 0.40 | 0.5 |
| | | 1 Month/40° C. | 0.09 | 0.1 |

Note:

Product impurity profile: Largest impurity - NMT 0.2% and Total impurity - NMT 1.0%

*The amount of mannitol in the formulation was decreased as the amount of the citric acid was increased to maintain the total weight of each unit.

Stability of Composition of Pitavastatin Calcium and Ezetimibe

The composition of pitavastatin calcium and ezetimibe prepared in Example 5 of the present disclosure were packed in Alu-alu blisters and stored under long term stability (25° C./60% RH). The assay of pitavastatin calcium and ezetimibe as well as the impurities were measured. The results are shown in the following Table 10 and Table 11.

TABLE 10

| Drug | Assay (%) | | | | |
|---|---|---|---|---|---|
| | Initial | 3 Months | 6 Months | 9 Months | 12 Months |
| Pitavastatin Ca | 98.2 | 96.4 | 97 | 95 | 96.5 |
| Ezetimibe | 100 | 99.5 | 101 | 102.9 | 99.7 |

TABLE 11

| Drug | Impurities | Impurities (%) | | | | |
|---|---|---|---|---|---|---|
| | | Initial | 3 Months | 6 Months | 9 Months | 12 Months |
| Pitavastatin Ca | Major | 0.02 | 0.03 | 0.09 | 0.08 | 0.05 |
| | Total | 0.02 | 0.03 | 0.09 | 0.13 | 0.05 |
| Ezetimibe | Major | 0.06 | 0.06 | 0.06 | 0.06 | 0.06 |
| | Total | 0.06 | 0.06 | 0.06 | 0.06 | 0.06 |

The above results indicate that the solid oral pharmaceutical composition provided by the present disclosure has excellent stability by adding suitable stabilizing agents.

Although the present disclosure has been explained in relation to its embodiment, it is to be understood that many other possible modifications and variations can be made without departing from the spirit and scope of the disclosure as hereinafter claimed.

What is claimed is:

1. A solid oral pharmaceutical composition, comprising:
   a first active ingredient, which is pitavastatin or a pharmaceutically acceptable salt thereof;
   a second active ingredient, which is ezetimibe or a pharmaceutically acceptable salt thereof;
   an alkaline stabilizing agent selected from the group consisting of magnesium oxide, magnesium aluminometasilicate, potassium hydroxide, sodium bicarbonate, sodium carbonate, sodium hydroxide, calcium carbonate, ammonium hydroxide, diethanolamine and a combination thereof;
   an acidic stabilizing agent selected from the group consisting of citric acid, acetic acid, tartaric acid, lactic acid, sodium phosphate monobasic and a combination thereof; and
   at least one excipient, selected from the group consisting of a diluent, a disintegrant, a binding agent, a sweetener, a lubricant, a glidant, a flavor, a coloring agent and a combination thereof;
   wherein a weight ratio of the first active ingredient to the alkaline stabilizing agent ranges from 20:1 to 1:1.

2. The solid oral pharmaceutical composition of claim 1, wherein the first active ingredient is pitavastatin calcium.

3. The solid oral pharmaceutical composition of claim 1, wherein the second active ingredient is ezetimibe.

4. The solid oral pharmaceutical composition of claim 1, wherein a loading of the first active ingredient in a unit dosage form is in a range from 0.5 mg to 5 mg.

5. The solid oral pharmaceutical composition of claim 1, wherein a loading of the second active ingredient in a unit dosage form is in a range from 5 mg to 20 mg.

6. The solid oral pharmaceutical composition of claim 1, which is a tablet.

7. The solid oral pharmaceutical composition of claim 6, which is a single layered tablet, wherein the single layered tablet comprises the first active ingredient, the second active ingredient, the alkaline stabilizing agent, the acidic stabilizing agent and the excipient.

8. The solid oral pharmaceutical composition of claim 6, which is a double layered tablet, wherein one layer of the double layered tablet comprises the first active ingredient, the alkaline stabilizing agent and the excipient, and the other layer of the double layered tablet comprises the second active ingredient, the acidic stabilizing agent and the excipient.

9. The solid oral pharmaceutical composition of claim 1, which is a capsule, wherein the capsule comprises a first tablet and a second tablet, the first tablet comprises the first active ingredient, the alkaline stabilizing agent and the excipient, and the second tablet comprises the second active ingredient, the acidic stabilizing agent and the excipient.

10. The solid oral pharmaceutical composition of claim 1, which is a capsule, wherein the capsule comprises a first granule and a second granule, the first granule comprises the first active ingredient, the alkaline stabilizing agent and the excipient, and the second granule comprises the second active ingredient, the acidic stabilizing agent and the excipient.

11. The solid oral pharmaceutical composition of claim 1, which is a capsule, wherein the capsule comprises a first pellet and a second pellet, and the first pellet comprises:
   a first core;
   a first drug-containing layer disposed on the first core and comprising the first active ingredient, the alkaline stabilizing agent and the excipient; and
   a first protection layer disposed on the first drug-containing layer and comprising a first polymer.

12. The solid oral pharmaceutical composition of claim 11, wherein the first polymer is povidone.

13. The solid oral pharmaceutical composition of claim 11, wherein the alkaline stabilizing agent is magnesium oxide.

14. The solid oral pharmaceutical composition of claim 11, wherein the second pellet comprises:
   a second core;
   a second drug-containing layer disposed on the second core and comprising the second active ingredient, the acidic stabilizing agent and the excipient; and
   a second protection layer disposed on the second drug-containing layer and comprising a second polymer.

15. The solid oral pharmaceutical composition of claim 14, wherein the second polymer is povidone.

16. The solid oral pharmaceutical composition of claim 14, wherein the acidic stabilizing agent is citric acid.

* * * * *